United States Patent
Bimman

[11] Patent Number: 5,833,691
[45] Date of Patent: Nov. 10, 1998

[54] APPARATUS AND METHOD FOR DRILLING STRICTLY ALIGNED HOLES IN BONES TO BE CONNECTED INTRAMEDULLARY NAILING

[76] Inventor: Lev A. Bimman, 2747 Del Medio Ct., #301, Mountain View, Calif. 94040

[21] Appl. No.: 890,913

[22] Filed: Jul. 10, 1997

[51] Int. Cl.[6] .................................................. A61B 17/56
[52] U.S. Cl. .............................................. 606/80; 606/96
[58] Field of Search ................................. 606/96, 97, 98, 606/86, 79, 80, 81, 82, 83, 84, 85, 62, 63, 64

[56] References Cited

U.S. PATENT DOCUMENTS

| | | | |
|---|---|---|---|
| 2,434,431 | 1/1948 | Pincock | 606/96 |
| 4,235,428 | 11/1980 | Davis | 606/96 |
| 4,722,331 | 2/1988 | Fox | 606/96 |
| 4,860,735 | 8/1989 | Davey et al. | 606/96 |
| 5,228,459 | 7/1993 | Caspari et al. | 606/96 |
| 5,409,493 | 4/1995 | Greenberg | 606/96 |
| 5,649,930 | 7/1997 | Kertzner | 606/96 |

*Primary Examiner*—Guy V. Tucker

[57] ABSTRACT

A device for coaxially drilling holes in fractured bones for intramedullary fixation includes of a frame (20) supporting a first V-shaped support (34) for a first part of a fractured bone and a second V-shaped support (56) for a second part of the fractured bone. The V-shaped supports are spaced from each other. The apparatus has a drilling head (28) with a calibrated pin (82) at the rear side of the drilling head (28). The drilling head is alternatingly installed in the aforementioned V-shaped supports (34 and 56) for drilling coaxial and strictly aligned holes in both parts of the fractured bone. The calibrated pin (82) has the same diameter as the drill bit (78) of the drilling head and is intended for insertion into the bone hole which is drilled first in order to support and align the drilling head (28) with the second part of the bone during drilling of the second hole. In operation, the surgeon supports the drilling head (28) with one hand and performs the feed of the bone toward the drill with another hand.

15 Claims, 3 Drawing Sheets

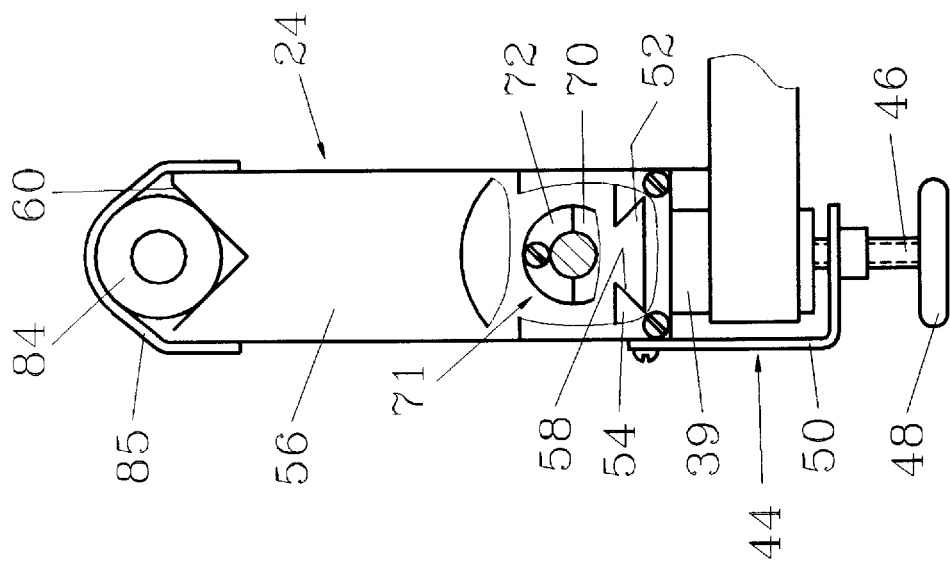
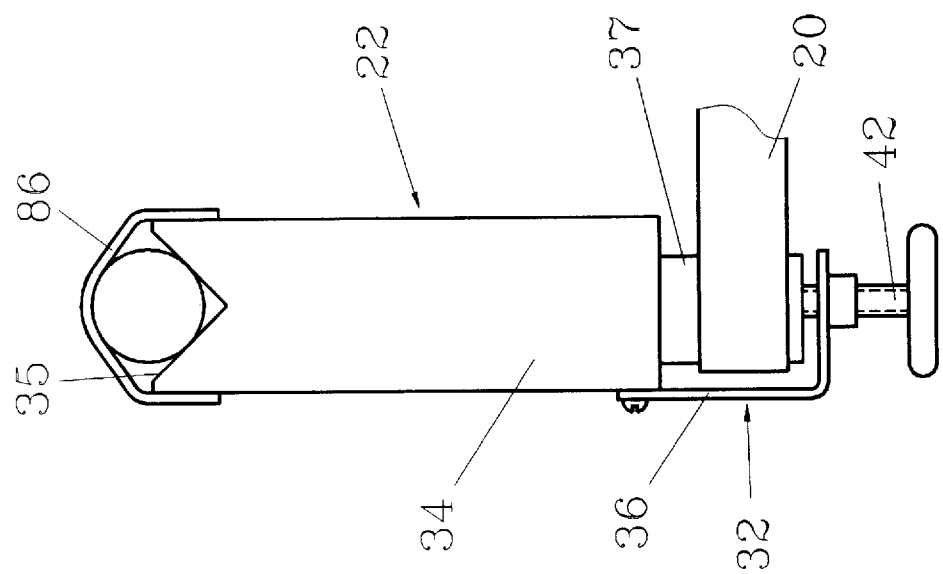

APPARATUS AND METHOD FOR DRILLING STRICTLY ALIGNED HOLES IN BONES TO BE CONNECTED INTRAMEDULLARY NAILING

FIELD OF THE INVENTION

The present invention relates to the field of surgery, and more particularly, to an apparatus and method for drilling strictly aligned holes in bones to be connected by intramedullary nailing.

BACKGROUND OF THE INVENTION

Intramedullary nailing or fixation is a method for holding a fractured bone in proper alignment by means of a metal pin or nail in the marrow cavity. This is normally performed by means of a steel spike inserted through the medually canal of a tubular bone to provide internal immobilization of fractures. Usually, intramedullary nailing fixation is utilized when there are no chances for the broken bones to grow together naturally.

In the opinion of specialists, for weight-bearing bones, intramedullary nailing is a fixation method superior to plates or external fixation, because the location of the rod in the intramedullary canal virtually guarantees proper axial alignment. Properly applied, an intramedullary fixation holds a fracture so securely that the patient can begin to move at once it is an important factor, because, as is known, with early movements the fracture diseases (such as stiffness and edema) are abolished. Other advantages of the intramedullary fixation are precise reduction and immediate stability of the fractured bones.

But in spite of all the advantages of the intramedullary fixation, this method is used seldom and surgeons try to avoid the use of this method. This is because the intramedullary fixation requires a very accurate axial alignment of fractured bone parts, i.e., an accurate alignment of holes for the insertion of the intramedullary nail into the bone parts to be interconnected.

In accordance with conventional practice such a drilling has to be performed with the aid of an X-ray apparatus for locating the precise position of the hole of the intramedullary nail before the drilling operation is started. In any case, it is extremely difficult to ensure strictly coaxial position of the holes in both parts of the broken bones, and the applicant is not aware of any efficient devices which are on the market and which could provide an efficient and reliable axial alignment of holes in mating parts of the broken bone.

Thus it is an object of the present invention to provide a simple, inexpensive and reliable apparatus for drilling strictly aligned holes in fractured bones to be connected by intramedullary nailing. Another object is to provide the aforementioned apparatus which is convenient in use and does not greatly depend on the skill of the surgeon. Still another object of the invention is to provide a method for drilling strictly aligned holes in fractured bones for connection by intramedullary nailing. These and other objects and advantages of the present invention will become apparent after the consideration of the ensuing description with the attached drawings.

BRIEF DESCRIPTION OF THE DRAWINGS

FIG. 3 is a view in a direction of arrow A in FIG. 1.

FIG. 4 is a fragmental view in the direction of arrow B in FIG. 1.

SUMMARY OF THE INVENTION

A device for coaxially drilling holes in fractured bones for intramedullary fixation consists of a frame supporting a first V-shaped support for a first part of a fractured bone and a second V-shaped support for a second part of the fractured bone. The V-shaped supports are spaced from each other. The apparatus has a drilling head with a calibrated pin at the rear side of the drilling head. The drilling head is alternatingly installed in the aforementioned V-shaped supports for drilling coaxial and strictly aligned holes in both parts of the fractured bone. The calibrated pin has the same diameter as the drill bit of the drilling head and is intended for insertion into the bone hole which is drilled first in order to support and align the drilling head with the second part of the bone during drilling of the second hole. In operation, the surgeon supports the drilling head with one hand and performs the feed of the bone toward the drill with another hand.

DETAILED DESCRIPTION OF THE INVENTION

Figure 1:
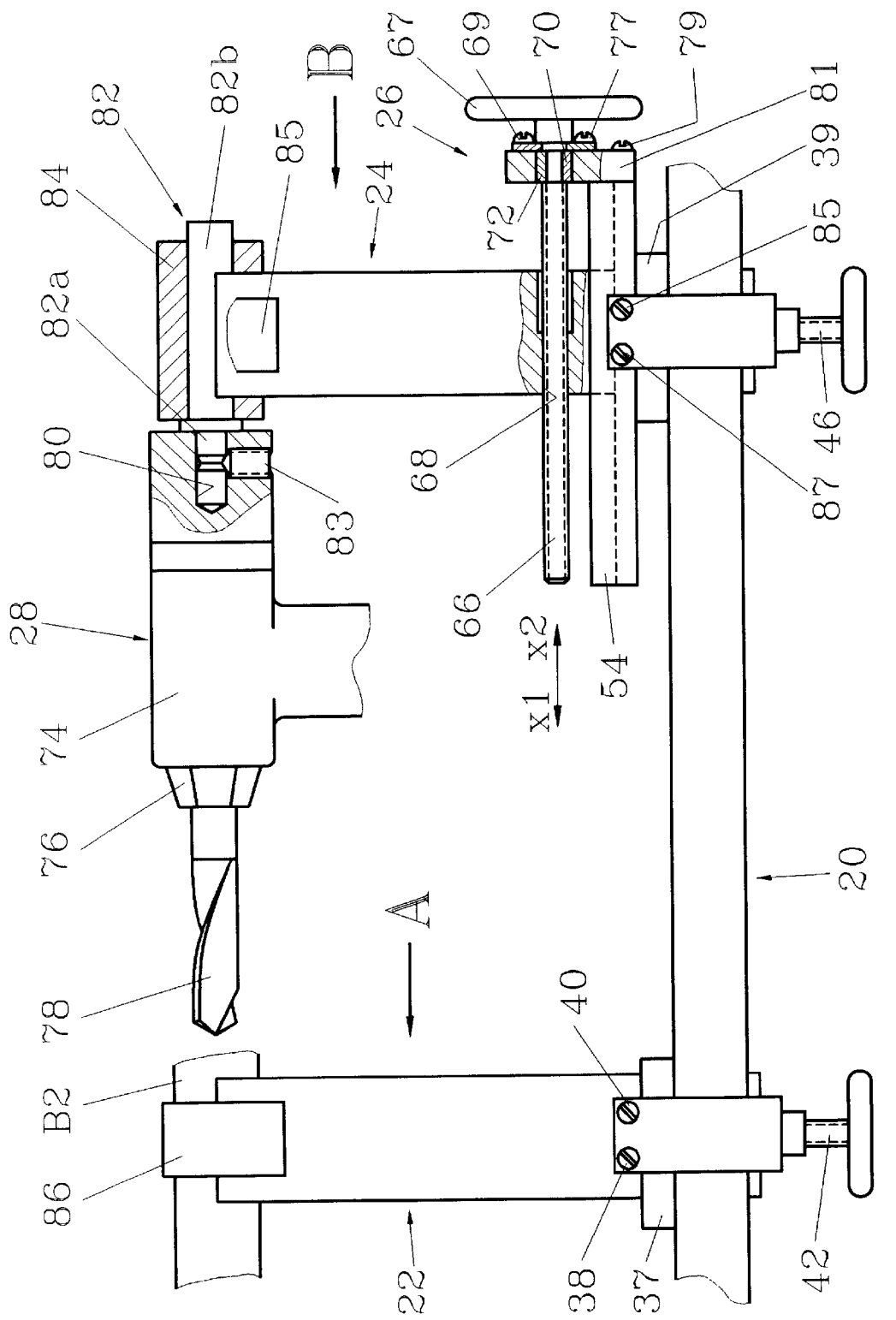
FIG. 1 is a side view, partially in section, of an apparatus of the invention in a position for drilling a hole in one part of the broken bone.
Figure 2:
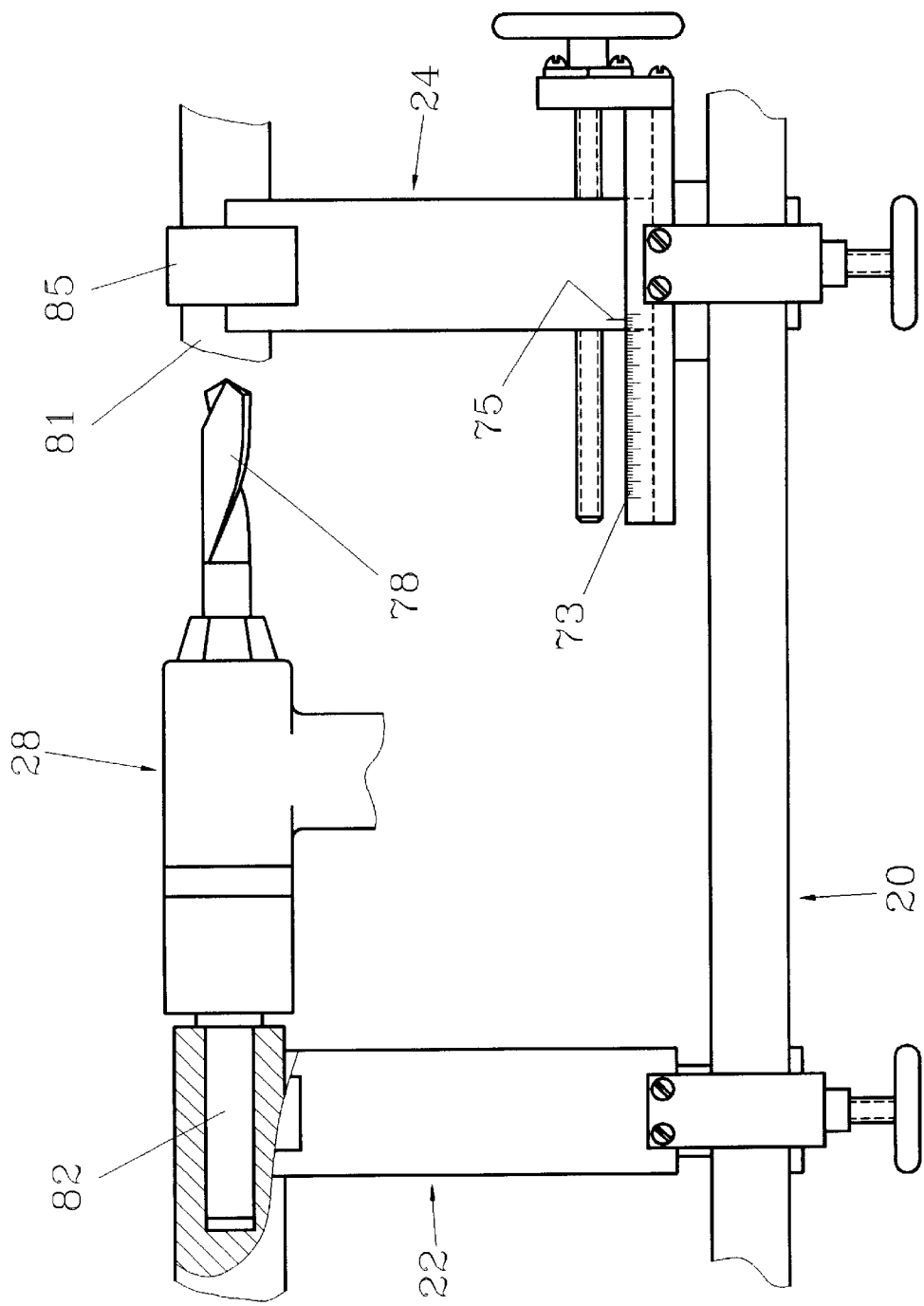
FIG. 2 is a side view, partially in section, of an apparatus of the invention in a position for drilling a hole in the other part of the broken bone.

The apparatus of the invention for drilling strictly aligned holes in bones to be connected by intramedullary nailing is shown in FIGS. 1 through 4, where FIG. 1 is a side view, partially in section, of the apparatus of the invention in a position for drilling a hole in one part of the broken bone. As can be seen from this drawing, the apparatus consists generally of a frame, e.g., in the form of a table 20 that supports a left carrier 22, a right carrier 26 with a feed mechanism 66, and a drilling head 28 alternatingly attachable to right carrier 24 or left carrier 22, as shown in FIGS. 1 and 2, respectively.

As shown in FIG. 3, which is a view in a direction of arrow A in FIG. 1, left carrier 22 has an L-shaped clamp 32 which is attached to table 20. Clamp 32 supports, on one end, a V-shaped block 34, which is attached to an L-shaped bracket 36 by screws 38 and 40 (FIG. 1) on one end, and a clamping bolt 42 which is screwed into bracket 36, on the other end so that an edge of table 20 is clamped between bolt 42 and V-block 34.

V-shaped block 34 has a V-shaped groove 35 on its upper surface. L-shaped clamp 32 allows clamping of left carrier 22 to the edge of table 20 in any longitudinal position of table 20. Vertical position of V-shaped groove 35 may be adjusted with the use of replaceable spacers 37 which are placed between V-shaped block 34 and the surface of table 20.

As shown in FIG. 4, which is a fragmental view in the direction of arrow B in FIG. 1, right carrier 26 is similar to left carrier 22 in that it has an L-shaped clamp 44 that has a clamping bolt 46 with a handle 48 in a lower portion 50 and a guide rail, e.g., a dovetail guide groove 58 on the upper surface of its upper portion 54. As shown in FIGS. 1 and 4, plate 54 with guide groove 58 has a flanged split bushing 71 which consists of an upper part 72 and a lower part 70. This bushing supports a lead screw 66 and prevents the screw from displacement in the axial direction.

Guide groove 58 slidingly supports a V-block 56 which has a guide rail 52 that engages guide groove 58 and is located at the bottom of V-block 56. A V-groove 60 is formed in the top surface of V-block 56. It should be noted that V-groove 60 of second carrier 26 is strictly aligned with V-shaped groove 35 of first carrier 22 in the direction parallel to the axial direction of table 20.

Vertical position of V-groove 60 is adjusted by means of a replaceable spacer 39 placed between upper portion 54 and the surface of table 20. Spacer 39 has the same thickness as spacer 37.

Lead screw 66 is screwed into a threaded hole 68 which passes in the longitudinal direction of the apparatus through V-block 56 so that rotation of the screw causes displacement of V-block 56 in the longitudinal direction of arrows X1 and X2 shown in FIG. 1.

Lead screw 66 has a handle 67 on its end protruding outwardly from bushing 71. The length of feed can be controlled by means of a scale 73 applied onto the side surface of upper portion 54 of L-shaped clamp 44 and an indicator mark 75 on moveable portion, i.e., on the side surface of second V-block 56.

Drill head 28 which is intended for drilling holes in the mating parts of fractured bones has a housing 74 that contains an angular reducer driven from a flexible shaft (not shown) and a collet chuck 76 for securing a drill bit 78. Such a drill head may comprise a conventional standard device for surgical purposes, e.g., a handpiece produced by Dyna-Dent, Division of Micromotor Corporation, Santa Ana, Calif., U.S.A. The drill head of this type may utilize drill bits of diameters within the range of about from 1.5 mm to 5 mm.

At the end opposite to chuck 76, housing 74 has an opening 80 strictly coaxial with the longitudinal axis of chuck 76 and hence of drill bit 78. Opening 80 serves to support a replaceable centering pin 82 which can be fixed by screw 83. Centering pin 82 has a tail portion 82*a* of the same diameter as hole 80 in the rear side of housing 74 and a calibrated portion 82*b* of the same diameter as drill bit 78. The latter supports a replaceable centering ring 84 for adjustment to the specific diameter of calibrated portion 82*b* and for supporting calibrated portion 82*b* and hence drill head 28 as a whole in V-groove 60 in a position strictly coaxial with the longitudinal axis of drill bit 78. In fact, centering ring 84 should have an outer diameter which approximately is equal to the outer cross-sectional dimension of the bone to be treated and is selected from a set of calibrating rings of different diameters.

The apparatus is provided with pieces of strong adhesive tapes 85 and 86 for fixing drill 28 and a bone to be treated in respective V-grooves 60 and 35.

Operation

First carrier 22 and second carrier 26 are first attached to table 20 by means of respective clamps 32 and 44, and the position of first V-groove 35 and second V-groove 60 is adjusted in the vertical direction by means of replaceable spacers 37 and 39.

Prior to drilling, centering pin 82 of the same diameter as drill bit 78 is installed into and fixed in drill head 28 by screw 83. Centering ring 84 is put onto calibrated portion 82*b* of the centering pin 82 and is placed into V-shaped groove 60 where it is secured by a strong adhesive tape 85. The use of the strong adhesive tape is preferable because it allows quick fixation to and removal of the bone from the respective V-block. This is essential for shortening the time of operation. The use of the tape is possible also because of relatively small dimensions and weight of the device as a whole.

Drilling head 28 holds drill bit 78 selected in accordance with the size of the bone and the size of a device selected for internal fixation of the broken bone.

For drilling holes in two parts of a broken bone separated by open fracture, one part B1 of the bone is moved aside and a second part B2 of the bone is placed into V-groove 35 and is fixed in it, e.g., by means of an adhesive tape 86. Muscles around the bone are moved aside to clear the access to the end face of the fractured bone. The surgeon is then switches on drill head 28 which has been secured by placing calibrating ring 84 into V-groove 60 of block 56 and fixing it by means of an adhesive tape 85. As drill bit 78 rotates, the surgeon feeds it toward the end face of bone part B2 by rotating handle 67 of lead screw for drilling an appropriate hole. Drilling experiences a very low resistance since the interior of the bone is a bone cavity. The feed is carried out by rotating handle 67. The depth of the hole is controlled by observing positions of indicator mark 75 with respect to scale 73.

When drilling of the hole in one part of the broken bone is completed, the surgeon moves second carrier 26 back to withdraw drill bit 78 from the bone. Drilling head 28 is then removed from second carrier 26 by peeling off adhesive tape 85, and calibrated portion 82*b* of centering pin 82 which has the same diameter as the diameter of the just drilled hole is inserted into this hole in the bone. As a result, drill head 28 assumes a position shown in FIG. 2. First part B1 of the fractured bone is then placed into V-groove 60 and is fixed in it by means of an adhesive tape 88. The muscles are moved aside in order to clear an access to the end face of bone part B1, the drill head is switched on, and the surgeon supports drill head 28 with one hand and feeds second carrier 26 with bone part B1 toward drill bit by rotating handle 67 of lead screw 66 with another hand. The depth of drilling is checked by means of indicator mark 73 and scale 73.

Upon completion of drilling of the second hole, the surgeon withdraws the drill bit from the hole drilled in bone part B1, and the intramedullary fixation is then carried out in an appropriate manner with the use of two strictly aligned holes in two parts of the fractured bones to be interconnected.

Thus it has been shown that the invention provides for a simple, inexpensive and reliable apparatus for drilling strictly aligned holes in parts of fractured bones to be connected by intramedullary nailing. The apparatus is convenient in use and does not greatly depend on the skill of the surgeon. The invention also provides a method for drilling strictly aligned holes in the parts of a fractured bone to be connected by means of intramedullary nailing.

Although the invention has been shown and described with reference to specific examples, it is understood that these examples should not be construed as limiting the scope of application of the present invention and that many modifications and changes are possible with regard to the steps of the method as well as the shape, configurations, materials, and dimensions of the parts and units of the drilling apparatus, provided they do not depart from the scope of the attached patent claims. For example, a hole can be first drilled in the bone part which has been treated second. Positions of the first and second carrier can be reversed. The bones can be fixed in V-grooves by means of a clamp with bolts. The feed mechanism may be associated with the first carrier, or feed mechanisms may be provided on both carriers. The feed may be carried out from an electrically or hydraulically driven mechanism. The feed may be carried out by means of a pinion and a tooth rack mechanism. The carriers may be attached to a table or to any other frame member by means other than L-clamps. The tail portion 82*a* can be fixed in drill head housing by a ball-type locking mechanism. The indicator mark may be located on the guide rail and the scale may be applied to the moveable part. The sequence of operation may be changed, e.g., first one part the bone is fixed in the device, the second part of the bone and muscles around the area of treatment are moved aside, the device is adjusted in a vertical direction, and the drill head is fixed in the V-block.

I claim:

1. A method for drilling strictly aligned holes in parts of a fractured bone to be connected by intramedullary nailing, comprising the steps of:

providing a drilling apparatus having: a frame; a first V-block with a V-groove; a second V-block with a second V-groove strictly aligned in the longitudinal direction of the apparatus with said first V-groove, means for attaching said first V-block to said frame; means for attaching said second V-block to said frame; and a drilling head alternatingly installable in said V-shaped grooves, said drilling head having a drill bit of a predetermined diameter on one end and a calibrated pin of the same diameter as said drill bit on the other end;

placing one part of said fractured bone into either one of said first V-groove and second V-groove;

fixing said either one part of said fractured bone in said either one of said first V-groove and said second V-groove;

fixing said drilling head in another of said first V-groove and second V-groove so that said drill bit is axially aligned with said either one part of said fractured bone;

drilling a first hole of a predetermined depth in said either one part of said fractured bone by feeding said drilling head toward said either one part of said fractured bone;

withdrawing said drill bit from said first hole;

disconnecting said drilling head from said another of said first V-groove and second V-groove;

placing another of said parts of said fractured bone into said another of said first V-groove and second V-groove;

inserting said calibrated pin into said first hole;

supporting said drilling head by one hand and feeding said another of said parts of said fractured bone toward said drill bit by another hand;

drilling a second hole of the same diameter as said first hole in said another of said parts of said fractured bone; and withdrawing said drill bit from said second hole.

2. The method of claim 1, further including the step of adjusting positions of said first-V-groove and said second V-groove by utilizing replaceable spacers which are placed between said means for attaching said first V-block and said frame and said means for attaching said second V-block and said frame, respectively.

3. A method for drilling strictly aligned holes in parts of a fractured bone to be connected by intramedullary nailing, comprising the steps of:

providing a drilling apparatus having: a frame; a first V-block with a V-groove; a second V-block with a second V-groove strictly aligned in the longitudinal direction of the apparatus with said first V-groove; means for attaching said first V-block to said frame; means for attaching said second V-block to said frame; and a drilling head alternatingly installable in said V-shaped grooves, said drilling head having a drill bit of a predetermined diameter on one end and a calibrated pin of the same diameter as said drill bit on the other end;

placing one part of said fractured bone into said first V-groove;

fixing said one part of said fractured bone in said first V-groove;

fixing said drilling head in said second V-groove so that said drill bit is axially aligned with said one part of said fractured bone;

drilling a first hole of a predetermined depth in one part of said fractured bone by feeding said drilling head toward said one part of said fractured bone;

withdrawing said drill bit from said first hole;

disconnecting said drilling head from said second V-groove;

placing another part of said fractured bone into said second V-groove;

inserting said calibrated pin into said first hole;

supporting said drilling head by one hand and feeding said another part of said fractured bone toward said drill bit by another hand;

drilling a second hole of the same diameter as said first hole in said another part of said fractured bone; and withdrawing said drill bit from said second hole.

4. The method of claim 3, further including the step of adjusting positions of said first V-groove and said second V-groove by utilizing replaceable spacers which are placed between said means for attaching said first V-block and said frame and said means for attaching said second V-block and said frame, respectively.

5. The method of claim 4 wherein said step of fixing said one part of said fractured bone in said first V-groove is carried out with the use of an adhesive tape.

6. The method of claim 5 wherein said step of fixing said drilling head in said second V-groove is carried out by using a calibrating ring which is placed onto said calibrated pin and is selected from a set of calibrating rings of different diameters by choosing a calibrating ring of a diameter essentially equal to the diameter of the bone being treated.

7. The method of claim 5 wherein said calibrated pin is selected with the same diameter as said drill bit.

8. An apparatus for drilling strictly aligned holes in bones to be connected by intramedullary nailing, comprising:

a frame having a longitudinal direction;

a first carrier rigidly attached to said frame with means for adjustably securing said first carrier to said frame in said longitudinal direction;

a first V-block rigidly supported by said first carrier and having a first V-groove on the top surface;

guiding means on said frame that extends in said longitudinal direction;

a second carrier having means for adjustably securing said second carrier to said frame;

said means for adjustably securing said second carrier having guiding means for slidingly guiding along said guiding means of said frame in said longitudinal direction and feeding means for feeding said second carrier towards and away from said first carrier;

a second V-block rigidly supported by said second carrier and having a second V-groove on the top surface; and a drilling head having a chuck for securing a drill bit of a predetermined diameter arranged in said longitudinal direction on one end of said drilling head and a calibrated pin arranged coaxially with said drill and extending in the opposite direction to said drill bit on the other end of said drilling head, said calibrated pin having the same diameter as said drill bit and supporting a replaceable centering ring for centering said calibrated pin in said second V-groove.

9. The apparatus of claim 8 having means for adjusting said first V-groove and said second V-groove in a vertical position with respect to said frame, said adjusting means being replaceable spacers.

10. The apparatus of claim 9, further including means for securing bones to be treated in said first V-groove and said second V-groove.

11. The apparatus of claim 10 wherein said means for securing bones are adhesive tapes.

12. The apparatus of claim 9 wherein said means for adjustably securing said first carrier to said frame in said longitudinal direction is an L-shaped clamp which has an L-shaped body that supports a clamping bolt on one end and rigidly supports said first V-block on the other end so that an edge of said frame is clamped between said bolt and said first V-block.

13. The apparatus of claim 8 wherein said feeding means for feeding said second carrier towards and away from said first carrier comprises: a lead screw which is arranged in said longitudinal direction and is rotationally supported by said frame; and a threaded opening which is formed in said second carrier and engages said lead screw so that rotation of said lead screw causes displacement of said second carrier in said longitudinal direction.

14. The apparatus of claim 13 wherein said feeding means is further provided with means for measuring the amount of feed in the form of a scale on said frame and an indicator mark on said second carrier which is readable with respect to said scale.

15. The apparatus of claim 8, further including means for securing said centering ring in said second V-groove, said means for securing said centering ring in said second V-groove being an adhesive tape.

\* \* \* \* \*